United States Patent
DiUbaldi et al.

(10) Patent No.: US 8,880,173 B2
(45) Date of Patent: Nov. 4, 2014

(54) DEVICE FOR PROVIDING TRANSDERMAL ELECTRICAL STIMULATION AT AN ADJUSTABLE POSITION ON A HEAD

(71) Applicants: Anthony R. DiUbaldi, Jackson, NJ (US); Jeyakumar Subbaroyan, Menlo Park, CA (US); Tamara C. Baynham, Valencia, CA (US)

(72) Inventors: Anthony R. DiUbaldi, Jackson, NJ (US); Jeyakumar Subbaroyan, Menlo Park, CA (US); Tamara C. Baynham, Valencia, CA (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 13/796,883

(22) Filed: Mar. 12, 2013

(65) Prior Publication Data
US 2014/0277324 A1   Sep. 18, 2014

(51) Int. Cl.
*A61N 1/04* (2006.01)
(52) U.S. Cl.
CPC .................. *A61N 1/0472* (2013.01)
USPC .......................................................... 607/39
(58) Field of Classification Search
CPC .................................................... A61N 1/0472
USPC ................................................. 607/139–141
See application file for complete search history.

(56) References Cited

U.S. PATENT DOCUMENTS

| | | | |
|---|---|---|---|
| 3,620,219 A * | 11/1971 | Barker | 607/139 |
| 5,569,166 A | 10/1996 | Stone | |
| 6,132,392 A | 10/2000 | Stone | |
| 6,275,736 B1 * | 8/2001 | Kuzma et al. | 607/57 |
| 6,735,475 B1 | 5/2004 | Whitehurst et al. | |
| 6,954,668 B1 | 10/2005 | Cuozzo | |
| 7,089,054 B2 | 8/2006 | Palti | |
| 7,155,276 B2 | 12/2006 | Lamont | |
| 7,231,256 B2 | 6/2007 | Wahlstrand et al. | |
| 7,277,749 B2 | 10/2007 | Gordon et al. | |
| 7,499,752 B2 | 3/2009 | Maschino et al. | |
| 7,610,095 B2 | 10/2009 | Naisberg | |
| 7,613,519 B2 | 11/2009 | Ridder | |
| 7,711,432 B2 | 5/2010 | Thimineur et al. | |

(Continued)

FOREIGN PATENT DOCUMENTS

| | | |
|---|---|---|
| EP | 2092951 | 8/2009 |
| WO | 2008/128215 | 10/2008 |

(Continued)

OTHER PUBLICATIONS

Johnstone et al., "Occiptial Nerve Stimulation for the Treatment of Occipital Neuralgia—Eight Case Studies," Neuromodulation, (2006) vol. 9, No. 1, pp. 41-47.

(Continued)

*Primary Examiner* — Amanda Patton
(74) *Attorney, Agent, or Firm* — Cohen & Hildebrand, PLLC

(57) ABSTRACT

A device for providing transdermal electrical stimulation at an adjustable position on a head. The device including a supporting member economically shaped and configured to be fixedly supported about an anatomical body part; the supporting member being adjustably positionable in only two directions substantially perpendicular to one another. No electrical stimulation is provided by the supporting member. Alternatively, the device includes at least one pair of electrodes for producing the transdermal electrical stimulation to the head. The electrodes are mounted to a securing member shaped and configured to be releasably securable only about a plurality of strands of hair at a predetermined fixed orientation without being secured about any anatomical body part.

7 Claims, 17 Drawing Sheets

(56) References Cited

U.S. PATENT DOCUMENTS

| | | | |
|---|---|---|---|
| 7,769,461 | B2 | 8/2010 | Whitehurst et al. |
| 7,844,340 | B2 | 11/2010 | Pawlowicz |
| 7,853,321 | B2 | 12/2010 | Jaax et al. |
| 7,979,137 | B2 | 7/2011 | Tracey et al. |
| 8,000,812 | B2 | 8/2011 | Paolizzi et al. |
| 8,041,429 | B2 | 10/2011 | Kirby |
| 2004/0243206 | A1 | 12/2004 | Tadlock |
| 2005/0154419 | A1 | 7/2005 | Whitehurst et al. |
| 2006/0004423 | A1 | 1/2006 | Boveja et al. |
| 2006/0025387 | A1 | 2/2006 | Hochman |
| 2006/0035914 | A1 | 2/2006 | Hochman |
| 2006/0047316 | A1 | 3/2006 | Fischell et al. |
| 2006/0047325 | A1 | 3/2006 | Thimineur et al. |
| 2006/0064140 | A1 | 3/2006 | Whitehurst et al. |
| 2006/0095088 | A1 | 5/2006 | De Ridder |
| 2006/0111754 | A1 | 5/2006 | Rezai et al. |
| 2006/0206165 | A1 | 9/2006 | Jaax et al. |
| 2006/0206166 | A1 | 9/2006 | Weiner |
| 2006/0235484 | A1 | 10/2006 | Jaax et al. |
| 2008/0262566 | A1 | 10/2008 | Jaax |
| 2009/0210028 | A1 | 8/2009 | Rigaux et al. |
| 2010/0030299 | A1 | 2/2010 | Covalin |
| 2010/0049277 | A1 | 2/2010 | Wahlstrand et al. |
| 2010/0114191 | A1 | 5/2010 | Newman |
| 2010/0152808 | A1 | 6/2010 | Boggs |
| 2010/0204749 | A1 | 8/2010 | Thimineur et al. |
| 2011/0060382 | A1 | 3/2011 | Jaax et al. |
| 2011/0093033 | A1 | 4/2011 | Nekhendzy |
| 2011/0106220 | A1 | 5/2011 | DeGiorgio et al. |
| 2011/0112603 | A1 | 5/2011 | DeGiorgio et al. |
| 2011/0184489 | A1 | 7/2011 | Nicolelis et al. |
| 2011/0218589 | A1 | 9/2011 | DeGiorgio et al. |
| 2011/0218590 | A1 | 9/2011 | DeGiorgio et al. |
| 2011/0230701 | A1 | 9/2011 | Simon et al. |
| 2011/0264167 | A1 | 10/2011 | Poletto |
| 2011/0282129 | A1 | 11/2011 | Rigaux |

FOREIGN PATENT DOCUMENTS

| | | |
|---|---|---|
| WO | 2011/044173 | 4/2011 |
| WO | 2011/044176 | 4/2011 |
| WO | 2011/044178 | 4/2011 |
| WO | 2011/044179 | 4/2011 |

OTHER PUBLICATIONS

Drummond et al., "Electrical Stimulation Decreases Neuralgic Pain After Trigeminal Deafferentation," Cephalalgia (2008), vol. 28, pp. 782-785.

Singla et al., "Role of Transcutaneous Electric Nerve Stimulation in the Management of Trigeminal Neuralgia," J. of Neurosciences in Rural Practice (Jul.-Dec. 2011); vol. 2, No. 2, pp. 150-152.

Cooper et al., "Establishment of a Temporomandibular Physiological State with Neuromuscular Orthosis Treatment Affects Reduction of TMD Symptoms in 313 Patients," The Journal of Cranomandibular Practice, (Apr. 2008); vol. 26, No. 2, pp. 104-117.

deCiccio, Vincenzo, "Central Syntropic Effects Elicited by Trigeminal Proprioceptive Equilibrium in Alzheimer's Disease: A case Report," Journal of Medical Case Reports, (2012); vol. 6, No. 161, pp. 1-8.

DeGiorgio et al., "Pilot Study of Trigeminal Nerve Stimulation (TNS) for Epilepsy: A Proof-of-Concept Trial," Epilepsia, (2006); vol. 47, No. 7, pp. 1213-1215.

Herman et al., "Using Transcutaneous Electrical Nerve Stimulation to Prevent Postoperative Pain," JADA (May 2002); vol. 133, pp. 643-645.

Mousavi et al., "Comparison Between Efficacy of Imipramine and Transcutaneous Electrical Nerve Stimulation in the Prophylaxis of Chronic Tension-Type Headache: A Randomized Controlled Clinical Trial," J. Res. Med. Sci. (Jul. 2011); vol. 16, No. 7, pp. 923-927.

Yameen et al., "Efficacy of Transcutaneous Electrical Nerve Stimulation and its different modes in Patients With Trigeminal Neuralgia," J. Pak. Med. Assoc. (May 2011); vol. 61, No. 5, pp. 437-439.

Tayeb et al., "Successful! Treatment of Nummular Headache With TENS," Cephalalgia (2008); vol. 28, pp. 897-898.

Allais et al., "Non-Pharmacological Approaches to Chronic Headaches: Transcutaneous Electrical Nerve Stimulation, Laser Therapy and Acupuncture in Transformed Migraine Treatment," Neurol Sci. (2003); vol. 24, pp. S138-S142.

Rushton, D. N., "Electrical Stimulation in the Treatment of Pain," Disability and Rehabilitation (2002); vol. 24, No. 8, pp. 407-415.

Johnson, Mark I., "Transcutaneous Electrical Nerve Stimulation (TENS) and TENS-like devices: do they provide pain relief?", Pain Reviews (2001); vol. 8, pp. 121-158.

Thorsen et al., "Trigeminal Neuralgia: Sudden and Long-Term Remission With Transcutaneous Electrical Nerve Stimulation," Journal of Manipulative & Physiological Therapeutics (Jul.-Aug. 1997); vol. 20, No. 6, pp. 415-419.

Narouze et al., "Supraorbital nerve Electric Stimulation for the Treatment of Intractable Chronic Cluster Headache: A Case Report," Headache (Jul./Aug. 2000), pp. 1100-1102.

Young, Ronald F. M.D., "Electrical stimulation of the Trigeminal Nerve Root for the Treatment of Chronic Facial Pain," J. Neurosurg. (1995), vol. 83, pp. 72-78.

Paemeleire et al., "Occipital Nerve Stimulation for Headache Disorders," Neurotherapeutics: The Journal of the American Society for Experimental NeuroTherapeutics, (Apr. 2010), vol. 7, pp. 213-219.

Magis et al., "Occipital nerve Stimulation for Drug-Resistant Chronic Cluster Headache: A Prospective Pilot Study," Lancet Neurol. (2007); vol. 6, pp. 314-321.

Bartsch et al., "Neurostimulation Approaches to Primary Headache Disorders," Current Opinion in Neurology, (2009) vol. 22, pp. 262-268.

Burns et al., "Treatment of Medically Intractable Cluster Headache by Occipital Nerve Stimulation: Long-Term Follow-Up of Eight Patients," The Lancet (Mar. 31, 2007); vol. 369, pp. 1099-1106.

Saper et al., "Occiptial Nerve Stimulation for the Treatment of Intractable Chronic Migraine Headache: ONSTIM Feasibility Study," Cephalalgia, (2010); vol. 31, No. 3, pp. 271-285.

Schwedt et al., "Occiptial Nerve Stimulation for Chronic Cluster Headache and Hemicrania Continua: Pain Relief and Persistence of Autonomic Features," Cephalalgia (2006); vol. 26, pp. 1025-1027.

Trentmand et al., "Stimulation Ranges, Usage Ranges, and Paresthesia Mapping During Occipital Nerve Stimulation," Neuromodulation: Technology at the Neural Interface, (2008); vol. 11, No. 1, pp. 56-61.

\* cited by examiner

DEVICE FOR PROVIDING TRANSDERMAL ELECTRICAL STIMULATION AT AN ADJUSTABLE POSITION ON A HEAD

BACKGROUND OF THE INVENTION

1. Field of the Invention

The present invention is directed to providing non-invasive transdermal electrical stimulation and, in particular, providing non-invasive transdermal electrical stimulation at an adjustable position on a head for the treatment of headaches.

2. Description of Related Art

Chronic headaches cause debilitating pain that significantly hampers one's lifestyle. Conventional treatment for intractable chronic headaches, especially migraines, include pharmacological agents, magnetic neurostimulation and/or electrical neurostimulation. Pharamcological agents typically have undesirable adverse side effects such as nausea, dizziness, sleepiness, fatigue and muscle weakness.

As an alternative to pharmacological agents, non-invasive methods such as transcranial magnetic neurostimulation have also been utilized in the treatment of migraine headaches. U.S. Patent Application Publication No. 2006/0047316 discloses a System for the Treatment of Migraine Headaches employing a magnetic pulse system including a head unit connected to a table unit by a connecting cable. The head unit includes a conducting wire coil through which an electrical current is used to create a high intensity, short duration, magnetic pulse. When the head unit is placed next to the scalp, the strong magnetic field penetrates the skull producing an electrical current that stimulates the cerebral cortex. The accompanying circuitry and instrumentation undesirably make this conventional device bulky. To reduce the bulkiness associated with external stimulation devices, stimulation devices of significantly reduced size have been implanted in the body. Several such known techniques for the treatment of headaches using an implantable stimulator are discussed in the following issued U.S. Patents and U.S. Published Patent Applications: U.S. Pat. No. 7,711,432; U.S. Pat. No. 6,735,475; 2011/0060382; 2010/0204749; 2006/0235484; 2006/0206165; 2006/0206166; 2006/0064140; 2006/0047325. However, implantation is an invasive surgical procedure that requires the leads to be placed subcutaneously. As a result such implanted devices suffer from the following potential drawbacks: lead migration, painful stimulation and possible infection at the site in which the leads pass subcutaneously beneath the skin. Yet another disadvantage is revision surgery required to replace the battery associated with the implantable pulse generators.

It would therefore be desirable to develop a non-invasive transcutaneous electrical stimulation patch for eliciting paraesthesis and/or reducing pain associated with intractible chronic headaches that overcomes the aforementioned disadvantages associated with conventional stimulation systems.

SUMMARY OF THE INVENTION

One aspect of the present invention is directed to a device for providing transdermal electrical stimulation at an adjustable position on a bead. The device includes a supporting member ergonomically shaped and configured to be fixedly supported about an anatomical body part; the supporting member being adjustably positionable in only two directions substantially perpendicular to one another. No electrical stimulation is provided by the supporting member.

Another aspect of the present invention is directed to a device for providing transdermal electrical stimulation at an adjustable position on a head that includes at least one pair of electrodes for producing the transdermal electrical stimulation. The electrodes are mounted to a securing member shaped and configured to be releasably securable only about a plurality of strands of hair at a predetermined fixed orientation without being secured about any anatomical body part.

BRIEF DESCRIPTION OF THE DRAWING

The foregoing, and other features of the present invention will be more readily apparent from the following detailed description and drawings of illustrative embodiments of the invention wherein like reference numbers refer to similar elements throughout the several views and in which.

DETAILED DESCRIPTION OF THE INVENTION

Figure 1:
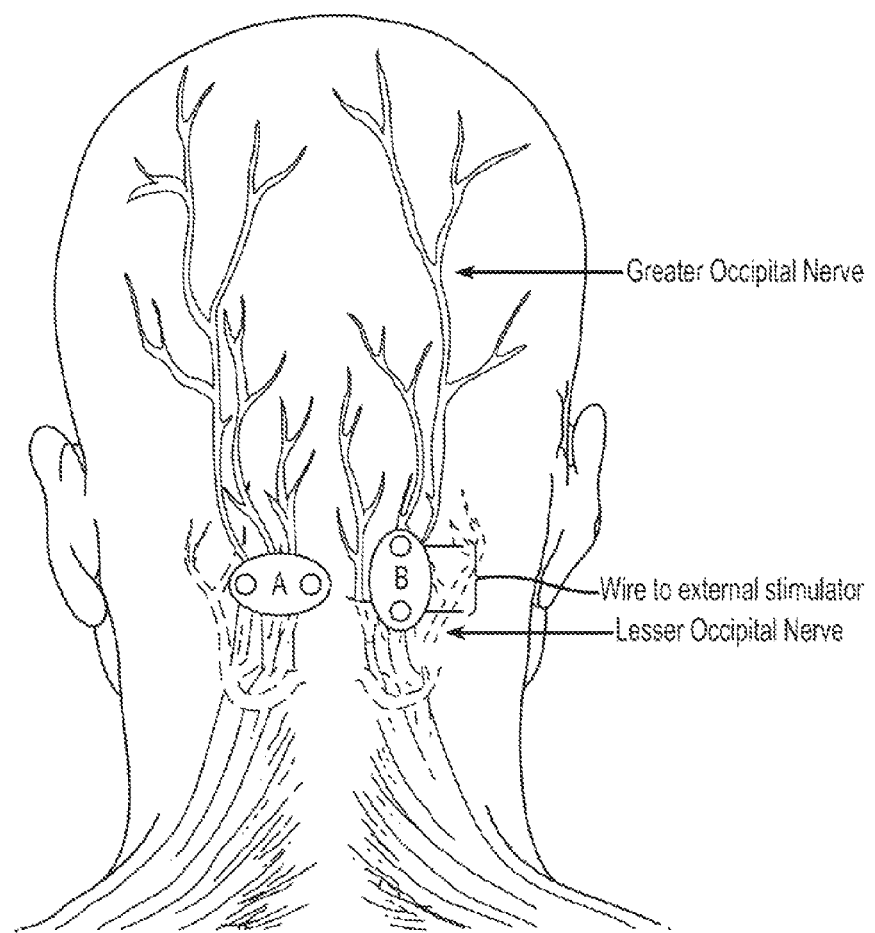
FIG. 1 is a back view of the head of the human body with two transcutaneous external electrical stimulator patches (electrical stimulator patch A and electrical stimulator patch B)
Figure 13:
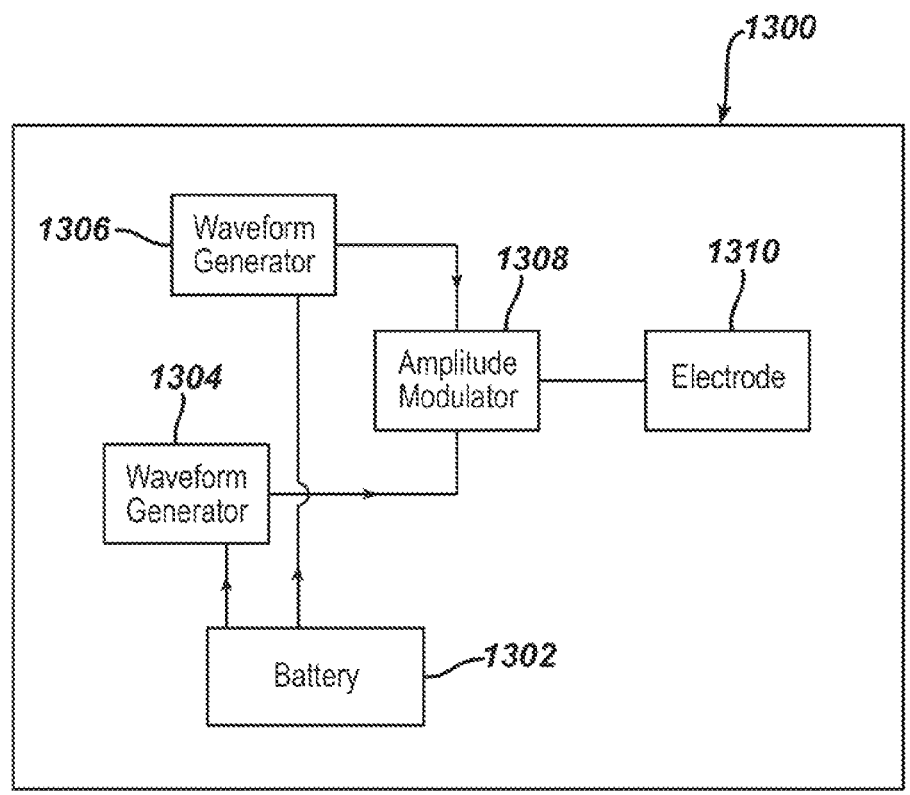
FIG. 13 is a schematic illustration of exemplary electronic circuitry associated with the transdermal electrical stimulation patch in accordance with the present invention.

FIG. 1 depicts two transcutaneous electrical stimulation patches positioned on the back of the head for occipital nerve stimulation. A first transcutaneous electrical stimulation patch "A" is positioned to stimulate the lesser occipital nerve or one of its branches. While a second transcutaneous electrical stimulation patch "B" is positioned to electrically stimulate the greater occipital nerve or one of its branches. Each of the transcutaneous electrical stimulation patches includes circuitry such as a waveform signal generator for generating the necessary electrical stimulation waveform, one or more pair of electrodes (one stimulating electrode and one returning electrode) and a power source (integrated into the patch). Alternatively, some of the electronic components (e.g., the waveform signal generator) and/or power source may be external to the patch and connected to the one or more electrodes via leads. FIG. 13 provides an exemplary schematic block diagram of the electronic circuitry associated with each transcutaneous electrical stimulation patch, described in detail hereafter. Preferably, the transcutaneous electrical stimulation patch is made of a flexible material that easily contours to the back of the neck and/or skull. The patch and/or the electrodes may be applied either unilaterally (one side of the body, right or left) or bilaterally (both left and right sides of the body). The waveform signal generator may be controlled by an external control device (not shown) using either a wired or wireless (e.g., infrared, radio frequency) communication interface.

Figure 11A:
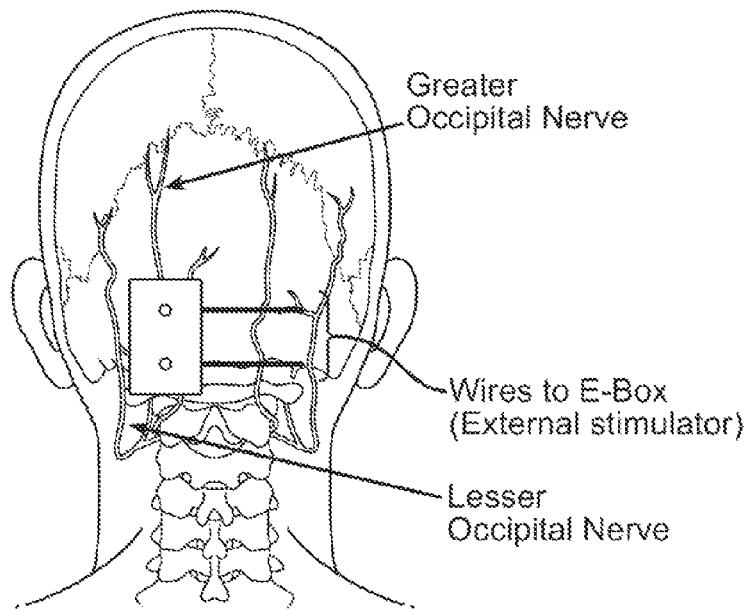
FIGS. 11A and 11B illustrate the transdermal electrical stimulation patch in accordance with the present invention for stimulation of the occipital nerve in a longitudinal or lateral arrangement, respectively.
Figure 11B:
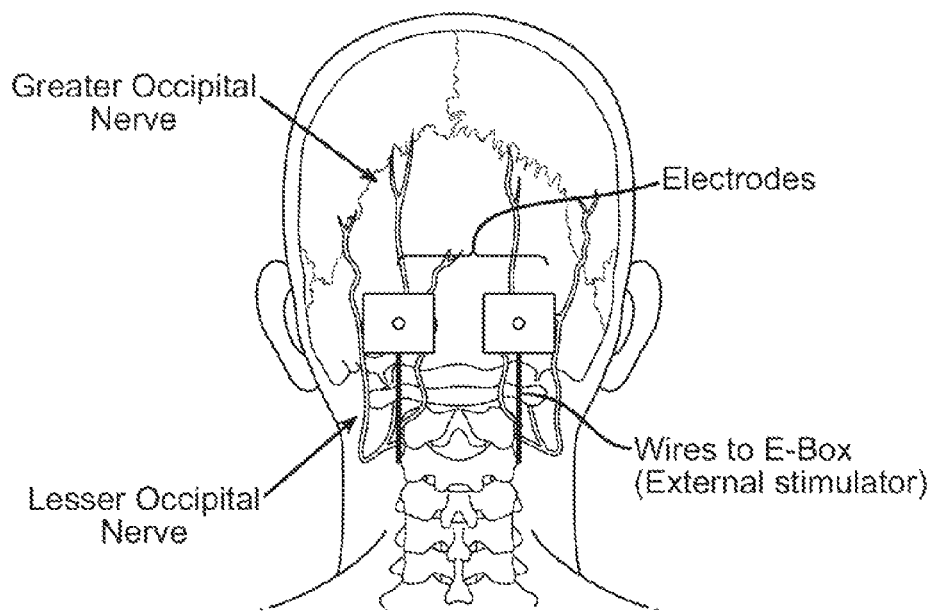

The patches may be oriented in any direction that induces paresthesia in the occipital nerve or one of its branches. Several exemplary orientations are illustrated in FIG. 1. Patch A is oriented in a lateral direction, while Patch B is arranged in a longitudinal direction. Despite being shown in different directions, patches A, B may both be oriented in the same direction, e.g., both in a lateral direction (one above the other) or both in a longitudinal direction (side-by-side). Multiple patches may be used in either a longitudinal arrangement (FIG. 11A) one above the other or a lateral arrangement (FIG. 11B) side-by-side.

Figure 2A:
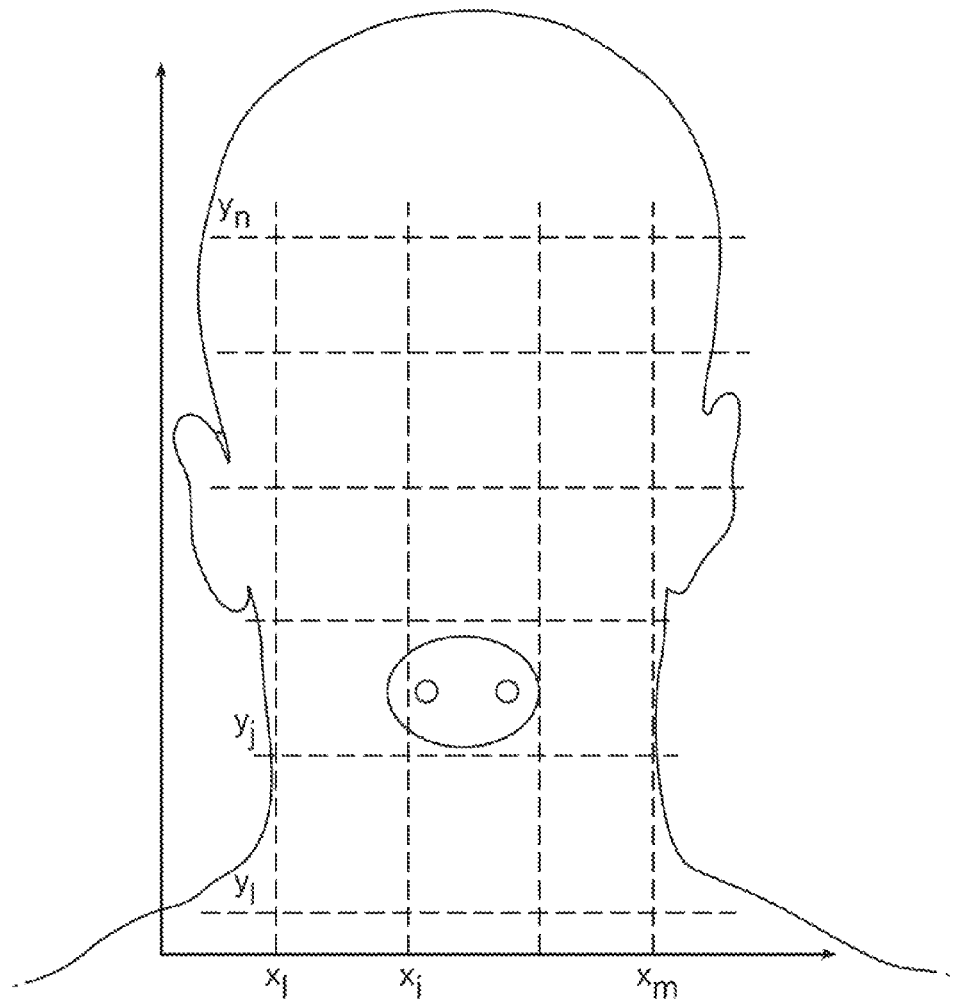
FIG. 2A is a full grid projected onto the back of the scalp/cervical/neck area of the human body.
Figure 2B:
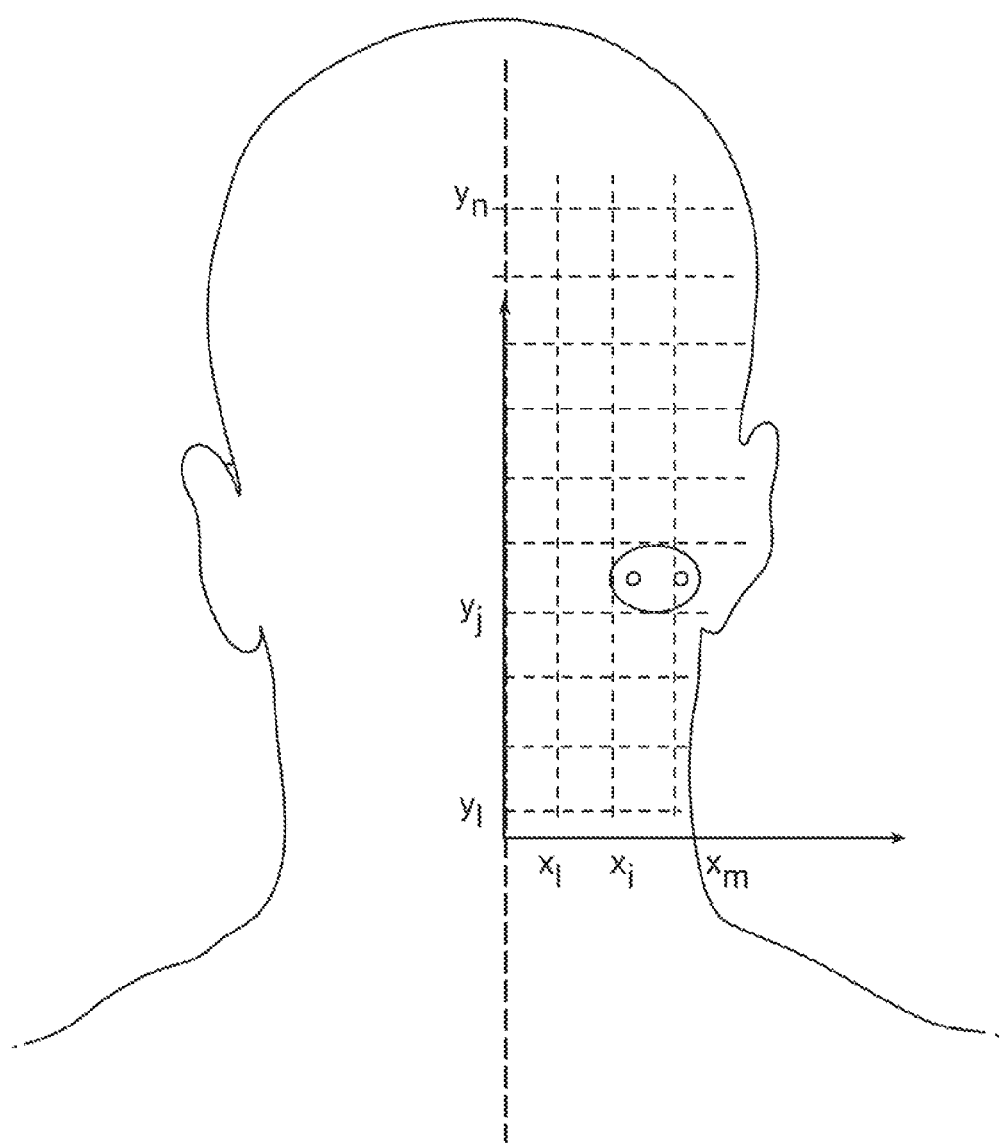
FIG. 2B is a right hand side half grid projected onto the back of the scalp/cervical/neck area of the human body.

Proper positioning of the transcutaneous electrical stimulation patch on the back of the patient's head in order to transcutaneously stimulate the occipital nerve or its branches may be realized by using a two dimensional (x, y) matrix or grid pattern projected onto the scalp/cervical/neck area of the patient as depicted in FIGS. 2A & 2B. The patient's head is shaved and the grid is projected onto the area. Instead of the grid covering completely the scalp/cervical/neck area (hereinafter referred to as a "full grid", as depicted in FIG. 2A), the grid may be projected only on to approximately half (right or left half) (hereinafter referred to as a "half grid") of the scalp/cervical/neck area (as illustrated in FIG. 2B). Of course, when using only a half-grid, the half-grid pattern may be interchangeably projected on either side of the head, depending on which side the patch is to be positioned.

A method for optimizing placement of a transcutaneous nerve stimulation device begins with identifying a plurality of test sites on a patient's head. Each block of the grid is a potential test site. The patch is placed at a selected location $(x_i, y_j)$ or a block of the grid and a test stimulation current signal is applied to elicit paresthesia and/or reduction in pain. An indicator of reduction in pain or paresthesia in response to the applied transcutaneous test current at the selected one of the plural test sites is recorded. The patch is then positioned at a new selected location $(x_i, y_j)$ or block of the grid and once again a test stimulation signal is applied. This procedure is repeated until the position (e.g., location or block) is identified in which the stimulating device elicits an optimum paresthesia and/or reduction in pain.

Figure 12:
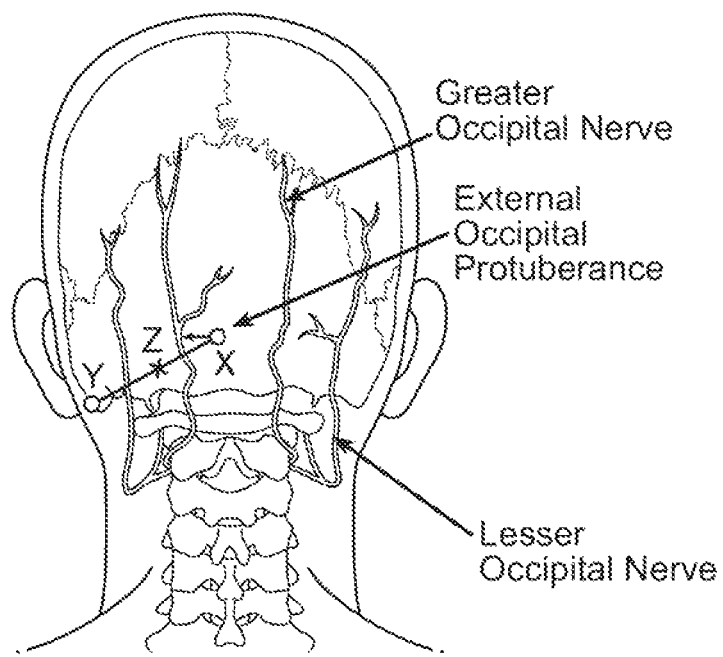
FIG. 12 illustrates several anatomical landmarks used to locate the superior nuchal line.

In a particular application of the method in accordance with the preceding paragraph, the electrodes in FIG. 1A are positioned on the scalp over the occipital nerve area. Proper positioning of the patch over the occipital nerve area may be realized using an anatomical landmark such as the external occipital protuberance. Specifically, a finger is run along the midline of the occipital bone (i.e., posterior, inferior skull) and locates the bony "bump" under the scalp identified by reference element "X" in FIG. 12. This spot can be indicated by placement of a skin marker or other identifying indicia (either permanent or temporary). Next the mastoid process is located by running a finger behind the patient's ear lobe and locating the lower margin of the bony "bump" where the sternocleidomstoid muscle attaches. Once again this spot may also be marked and is identified as reference element "Y." A straight line (superior nuchal line) is drawn connecting the two bony landmarks (X & Y). The approximate midpoint of the superior nuchal line is marked and identified in FIG. 12 as reference element "Z." The locating and marking of spots X, Y and Z will be repeated on the contra lateral side.

Releasable liners are removed from the stimulating electrodes to expose a releasable adhesive layer. A first electrode is positioned so that its center is substantially aligned over a midpoint of the superior nuchal line. A second electrode may be placed either beneath the first electrode or on the contra lateral side similar to the first electrode. Wire leads are snapped onto connector nipples associated with the electrodes. A negative lead is connected to the first electrode. The signal generator is powered on and an opposite end of the negative lead is connected to the signal generator. An initial voltage is preferably preprogrammed into the device. By way of example, the initial preprogrammed voltage is approximately 6 volts. Thereafter, the voltage is increased in predetermined steps or increments to deliver a signal of a predetermined average current (e.g., preferably approximately 70 mA average current). With each increment in voltage, the patient reports any discomfort. In the presence of any discomfort, the voltage is decremented in predetermined intervals (e.g., preferably approximately ½ volt steps) until the patient is no longer experiencing any discomfort. The following events are recorded: (i) stimulation voltage at which the subject first reports sensation (hereinafter referred to as a "perception threshold"); (ii) stimulation voltage at which the subject reports comfortable sensation (hereinafter referred to as "optimal stimulation"); (iii) maximum tolerable stimulation voltage when discomfort is experienced (hereinafter referred to as "discomfort threshold"); and (iv) x, y coordinates in the grid of sensation in the paresthesia map. The leads are disconnected from the signal generator which is reset to several different frequencies and the steps above repeated. Once this process has been completed for the first electrode, the process is repeated for the second electrode The grids in accordance with the embodiments in FIGS. 2A & 2B each require a projecting or imaging device to cast the grid onto the back of the scalp/cervical/neck area. In such configuration, the scalp is shaved to secure the stimulation patch to the skin using an adhesive. Alternatively, adjustable positioning head electrical stimulation devices in accordance with the present invention may instead be supported by one or more anatomical parts on the body without having to shave any part of the head.

Figure 3A:
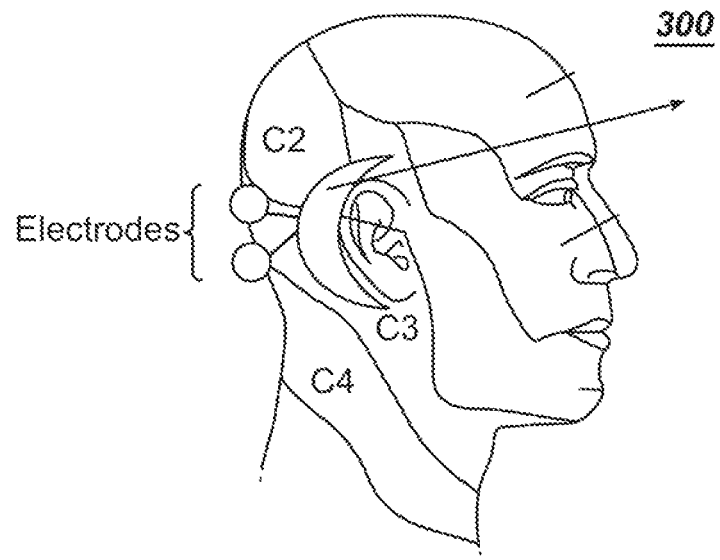
FIG. 3A is a side view of an occipital neurostimulator ear clip device worn about the right ear.
Figure 3B:
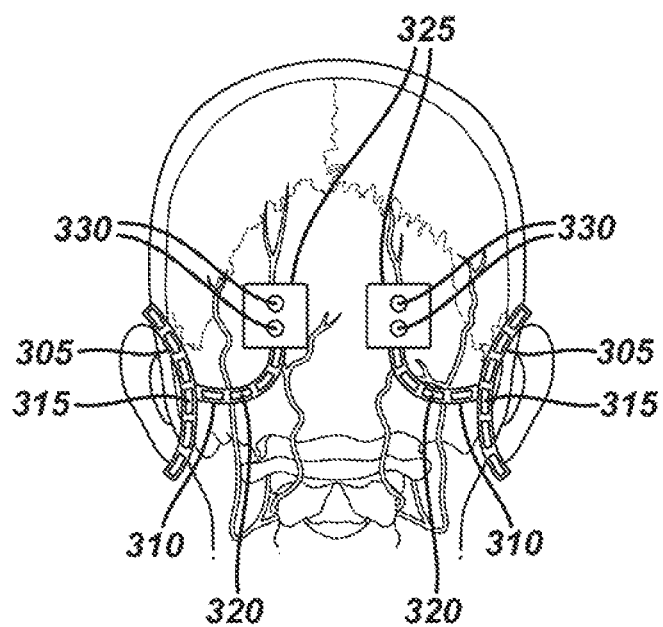
FIG. 3B is a back view of the occipital neurostimulator ear clip device worn about each ear.

A first exemplary adjustable positioning head electrical stimulation device 300, as depicted in FIG. 3A, is ergonomically shaped to be supported by and disposed about at least a portion of the outer contour of the ear. Referring to FIG. 3B, unilateral stimulation may be provided using ear clip adjustable positioning headset device 300 disposed about either the left ear or right ear, whereas bilateral stimulation may be realized by wearing the device on both ears simultaneously. Separate adjustable positioning headset devices may be designed specifically for one side of the body (e.g., left ear or right ear). It is, however, contemplated and within the intended scope of the present invention to design a universal ear clip shaped adjustable positioning headset device that is ergonomically designed to be interchangeably used with either the left ear or right ear.

Ear clip adjustable positioning headset device 300, as shown in FIGS. 3A and 3B, is preferably adjustable in two directions (e.g., an x-direction and a y-direction). This is accomplished by configuring device 300 to include a main arm 305, and an auxiliary arm 310. Main arm 305 has a plurality of slots 315 defined therein for adjusting in a substantially y-direction (substantially vertical direction) the positioning of the auxiliary arm 310. One end of the auxiliary arm 310 is supported within one of the slots 315. An opposite end of the auxiliary arm 310 supports or receives the stimulation patch 325. The patch is also adjustable in an x-direction (substantially horizontal direction) within a plurality of slots 320 defined within the auxiliary arm 310. Thus, the position of the stimulation patch 325 may be adjusted two dimensionally (in the y-direction by positioning one end of the auxiliary arm 310 within one of the slots 315 defined in the main arm 305, while adjustment in the x-direction is realized by selecting one of the plural slots 320 defined in the auxiliary arm 310). As described above with respect to the grid or matrix in FIGS. 2A & 2B, the ear clip adjustable positioning headset device 300 is positioned at a first location on the head with the stimulation patch 325 received within one of the slots 320 defined in the auxiliary arm 310 which, in turn, is received within one of the slots 315 defined in the main arm 305. A test stimulation signal is applied to elicit paresthesia and/or reduction in pain. Thereafter, the patch is positioned at a new location (a different slot 315 and/or slot 320) and once again a test stimulation signal is applied. This procedure is repeated until the stimulation patch is positioned at that location which elicits optimum paresthesia and/or reduction in pa response. Each of the electrodes 330 is disposed in a separate patch in accordance with FIG. 3A, whereas multiple electrodes 330 are integrated within a single patch 325 in FIG. 3B. Either configuration is contemplated and used interchangeably. Despite the fact that only a single auxiliary arm 310 is shown in FIGS. 3A and 3B as being associated with a main arm 305, more than one auxiliary arm may be associated with a main arm 305 to stimulate multiple locations simultaneously on the same side of the body. The electronic circuitry (e.g., waveform generator, processors, etc.) are preferably disposed within the main arm 305.

Figure 4A:
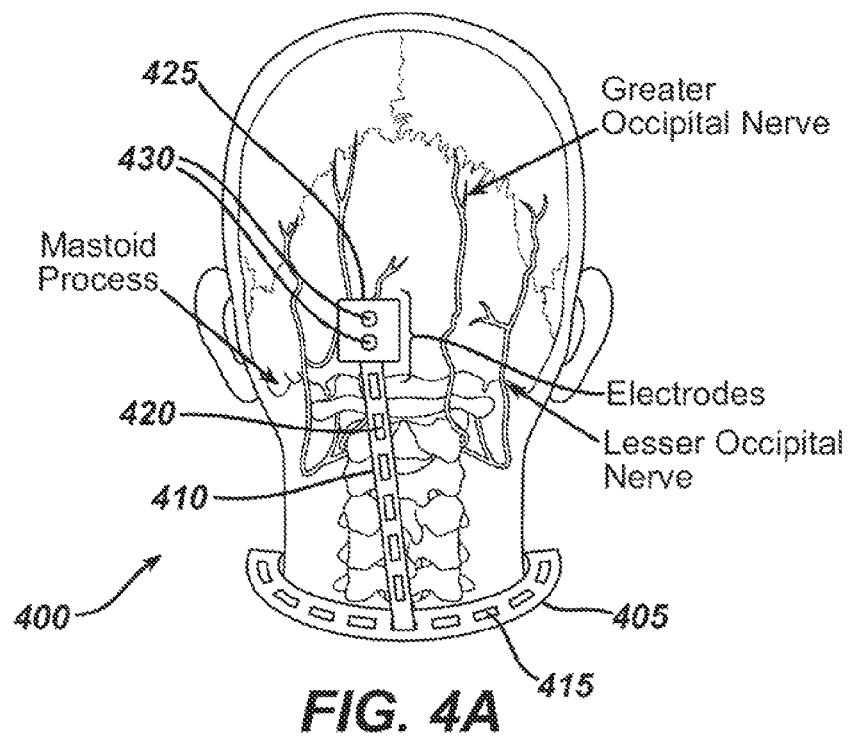
FIG. 4A is a back view of an occipital neurostimulator neck brace device with a pair of electrodes integrated into a single patch stimulating the lesser occipital nerve or branches thereof on the left band side of the body.
Figure 4B:
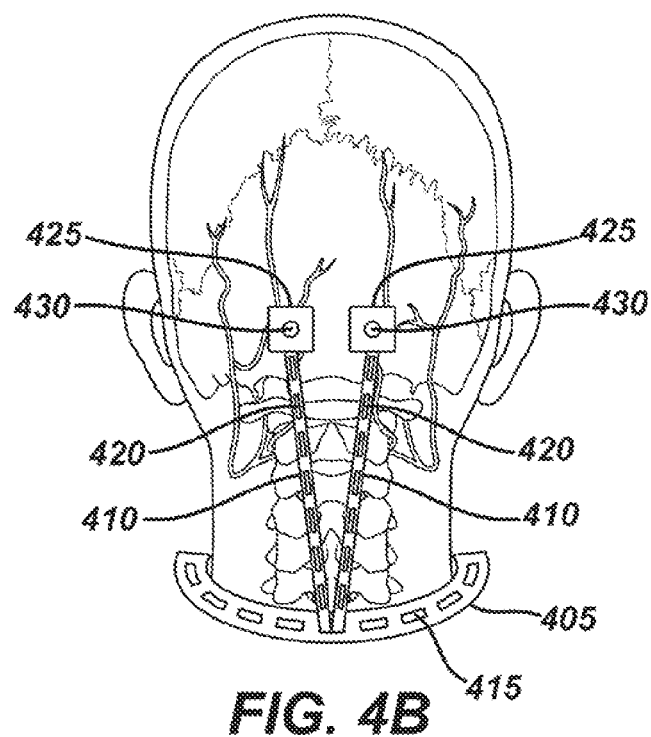
FIG. 4B is a back view of an occipital neurostimulator neck brace device with each electrode disposed in a separate patch positionable on the body independently of one another.

An alternative configuration of the adjustable positioning headset device 400 depicted in FIGS. 4A and 4B is disposed about at least a portion of the neck, rather than the ear. The electronic circuitry (e.g., waveform signal generator, processors, etc.) are preferably disposed within the main arm 405. One or more auxiliary arms 410 are releasable secured with one of a plurality of slots 415 defined within the main arm 405 in order to adjust in the substantially x-direction (substantially horizontal direction). Adjustment in the substantially y-direction (substantially vertical direction) is realized by adjustment of the stimulation patch 425 in one of the slots 420 defined in the auxiliary arm 410. Once again, plural electrodes 430 may be disposed within a single integrated patch, as illustrated in FIG. 4A. Alternatively, each electrode may be within its own separate patch, as shown in FIG. 4B. Any number of one or more auxiliary arms may be utilized, as desired.

Other configurations of the adjustable positioning headset devices supported by other body parts are contemplated that permit adjustment of positioning of the stimulation patch in at least one direction (e.g., adjustment of the stimulation patch relative to the auxiliary arm and/or adjustment of the auxiliary arm relative to the main arm), preferably two dimensional adjustment independently of one another. Regardless of the configuration, it is preferred to design the adjustable positioning headset device so as to be aesthetically and cosmetically inconspicuous.

The adjustable positioning head electrical transdermal stimulation devices described in the preceding paragraphs may be used to vary the position of the transdermal electrical stimulation patch on the head based on the induced paresthesia resulting from a test stimulation signal generated at a particular location similar to that of the projected grid pattern.

The aforementioned adjustable positioning head electrical transdermal stimulation devices have all been secured to an anatomical body part, e.g., about the ear or about the neck. Such devices are advantageously releasably securable to the body without having to shave all or a portion of the scalp while eliminating the need for adhesives. Alternative mechanical devices are contemplated that, rather than being supported by an anatomical body part, are releasably securable directly about a plurality of hair stands at a desired fixed, stationary location on the back of the patient's head. Several exemplary embodiments are shown and described herein in which the transdermal electrical stimulation device is releasably attachable only to one or more strands of hair on the head without the use of an adhesive or supported by an anatomical body part.

Figure 7A:
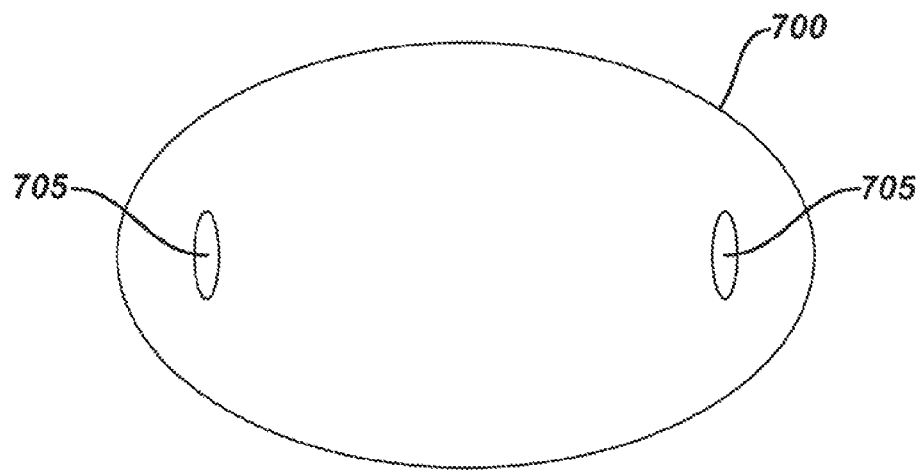
FIG. 7A is an exterior view of an exemplary electrical stimulation device securable about a plurality of strands of hair, rather than to an anatomical body part.
Figure 7B:
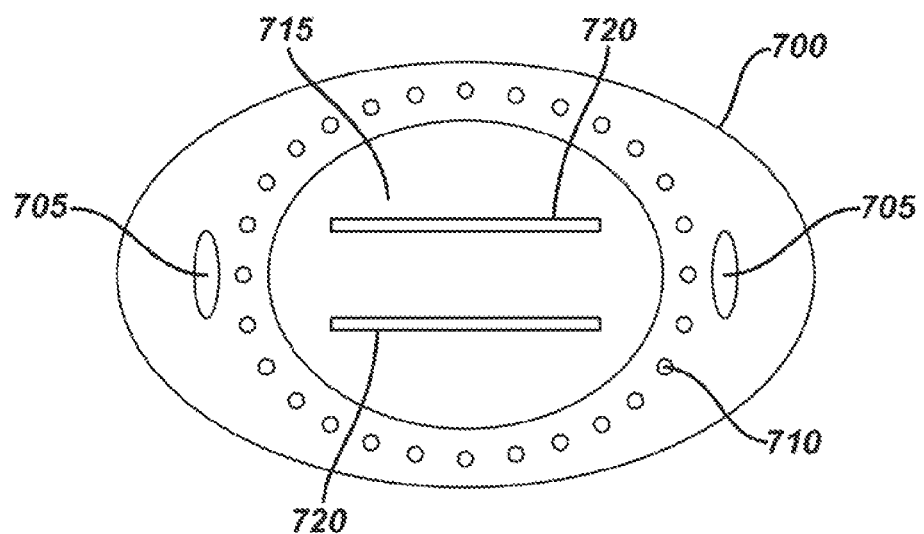
FIG. 7B is an interior view of the device of FIG. 7A.

In a first embodiment illustrated in FIGS. 7A and 7B depicting the exterior and interior surfaces, respectively, of a securing member 700 made of a flexible substrate with one or more openings 705 defined therein through which a clip, pin, rod, shaft, VELCRO® or other non-adhesive releasable securing mechanism is received to releasably secure the securing member about a plurality of strands or hair at a desired position on the back of the head to be electrically stimulated. A stimulation area 715 (e.g., transdermal electrical stimulation patch) is preferably centrally located within which one or more electrode pairs 720 are disposed. The size and shape of the stimulation area 715 may be modified, as desired, depending on the targeted site to be stimulated. A single stimulation area 715 is illustrated in FIG. 7B, however, more than one stimulation area may be provided. A plurality of non-conductive bristles, teeth or pins 710 assist exclusively in anchoring/securing the patch about the plural strands of hair, not to provide electrical stimulation or move the hair away to provide contact at the electrode/scalp interface. The one or more electrodes 720 in the stimulation area 715 are preferably tubular in shape and flexible so as to substantially conform to the shape of the head. Additional conducting material, e.g., hydrogel or conductive gel, is preferably provided proximate exposed tips of the electrodes or within a cavity of the tube shaped electrode. Upon application of sufficient force the conducting material is released from the cavity of the electrodes to increase conductivity at the electrode/scalp interface.

Figure 8A:
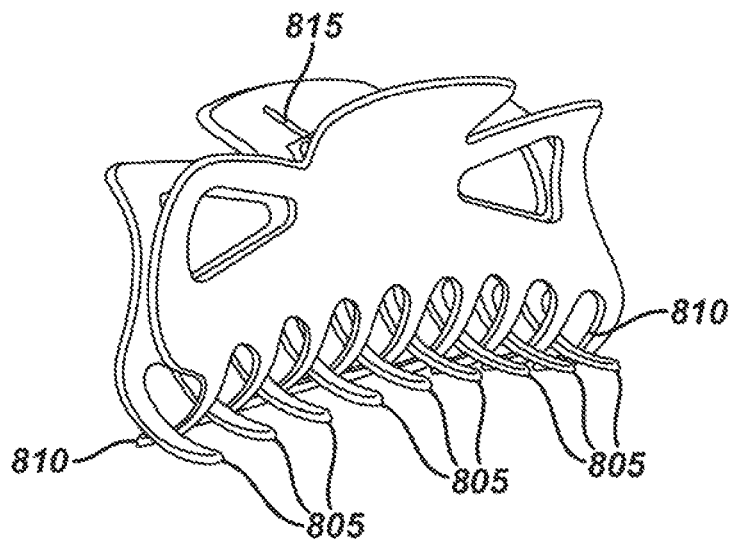
FIG. 8A is a perspective view of another exemplary electrical stimulation device to be secured about a plurality of strands of hair, rather than to an anatomical body part.
Figure 8B:
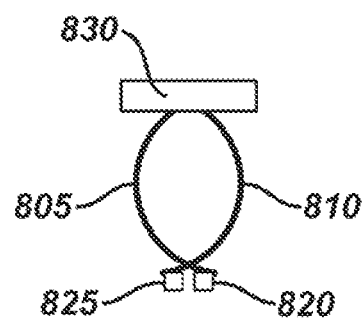
FIG. 8B is a cross-sectional view of the device of FIG. 8A.

A second exemplary embodiment is depicted in FIGS. 8A & 8B in which a butterfly hairclip 800 comprises a series of intermeshed mating teeth 805, 810, which by default, are retained in a clamped state by a spring 815. Proximate the ends of at least one, preferably all, the teeth 810, 805 are electrode pairs (e.g., anode 820 and cathode 825, respectively). These electrode pairs 820, 825 are electronically connected to electronic circuitry, e.g., printed circuit board with electronics 830, disposed at opposite ends of the respective teeth. Once the hairclip 800 is properly positioned on the head, it is anchored/secured about a plurality of hair strands by applying a counterbalancing force to the spring 815 and securing it in place when the force is removed. Electrode pairs may be disposed on all or only some of the teeth of the hairclip depending on the target site to be stimulated.

Figure 9:
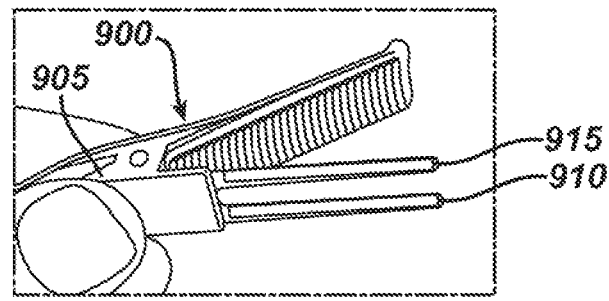
FIG. 9 is a perspective view of still another exemplary electrical stimulation device to be secured about a plurality of strands of hair, rather than to an anatomical body part.

Still another alternative hair securing mechanism is a hair clip 900 shown in FIG. 9 with a spring 905 for maintaining the clip in a normally closed position. A pair of electrode prongs (e.g., anode 910 and cathode 915) produce the electric field for stimulating the targeted area.

Figure 10A:
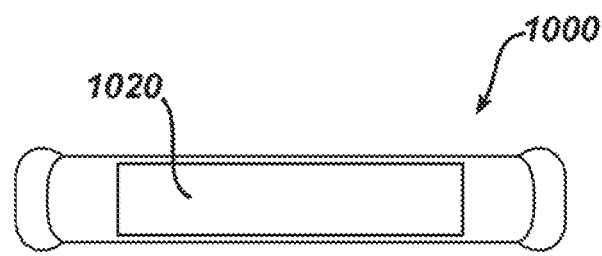
FIG. 10A is a top view of yet another exemplary electrical stimulation device to be secured about a plurality of strands of hair, rather than to an anatomical body part.
Figure 10B:
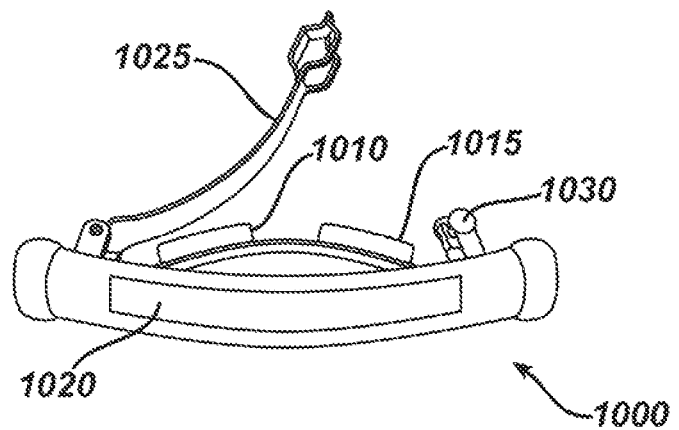
FIG. 10B is a side view of the device of FIG. 10A.

A barrette 1000 is depicted in FIGS. 10A & 10B, wherein the printed circuit board and associated electronic circuitry 1020 is provided to generate an electric field in a pair of electrodes (e.g., anode 1010, cathode 1015) disposed proximate the head. A hinged arm 1025 of the barrette 1000 is releasable secured by a locking mechanism 1030.

Other releasable hair securing mechanisms are contemplated and within the intended scope of the present invention provided that that are releasably securable about a plurality of hair strands and able to accommodate the electrodes and associated electronic circuitry for producing a desired electric field of sufficient are and strength to stimulate a target site on the head (e.g., stimulation of the occipital nerve).

Heretofore, the present invention has been shown and described as a neurostimulation device for treatment of chronic headaches by stimulating only the occipital nerve or one of its branches (ONS—occipital nerve stimulation) via one or more pairs of transdermal electrodes. However, ONS alone is limited to treatment of intractable occipital neuralgia and cervicogenic headaches associated with pain in the back of the head/neck while exhibiting reduced efficacy in response to front-temporal headaches (e.g., migraines, cluster headaches) associated with the front of the head. In such cases, localized stimulation of the occipital nerve or one of its branches alone has less than optimum impact on reducing or minimizing the front-temporal pain produced in the front of the head above the eyes. Localized stimulation of the occipital and trigeminal nerves and associated superficial branches in accordance with the present invention may be particularly well suited for the treatment of chronic headaches causing pain in the back as well as in the front of one's head. This alternative transcutaneous external electrical stimulator system in accordance with the present invention is illustrated in FIGS. 5A-5C.

Figure 5A:
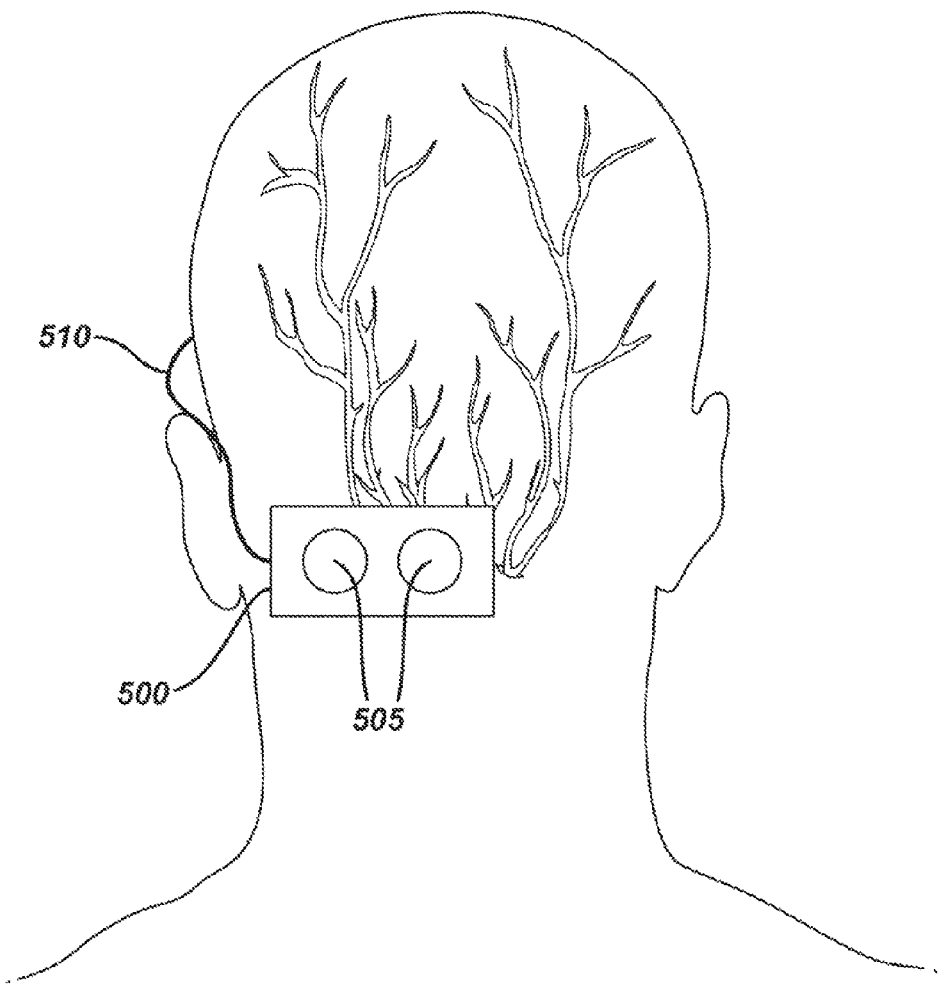
FIG. 5A is back view of the head of the human body showing an alternative embodiment of the present inventive transcutaneous external electrical stimulator system for simultaneous/staggered electrical stimulation of the occipital and trigeminal nerves with the patch disposed to stimulate the occipital nerve oriented in a substantially horizontal direction.
Figure 5B:
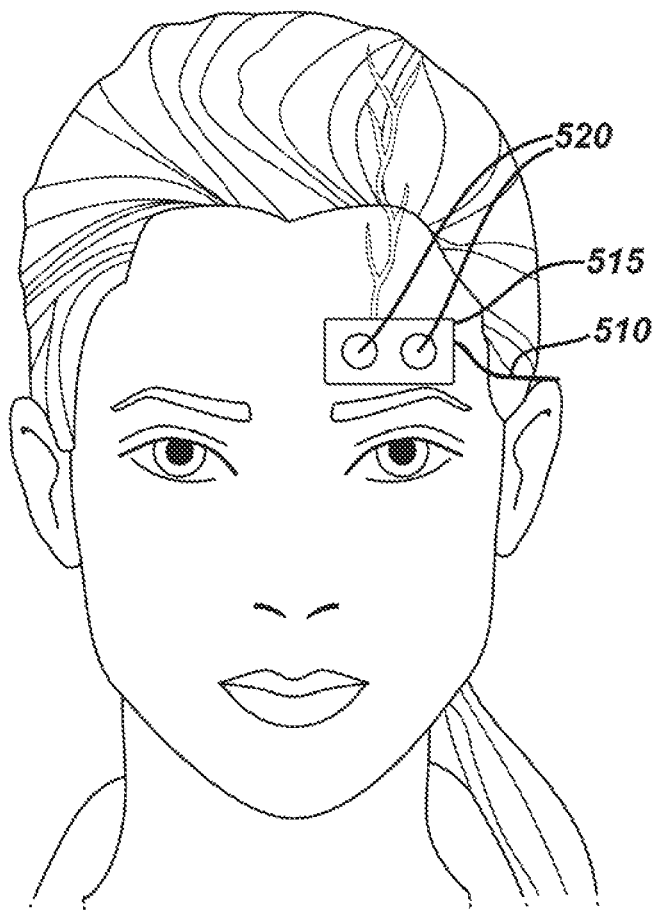
FIG. 5B is a front view of the present inventive transcutaneous external electrical stimulation system for simultaneous/staggered electrical stimulation of the occipital and trigeminal nerves with the patch disposed to stimulate the trigeminal nerve oriented in a substantially horizontal direction.
Figure 5C:
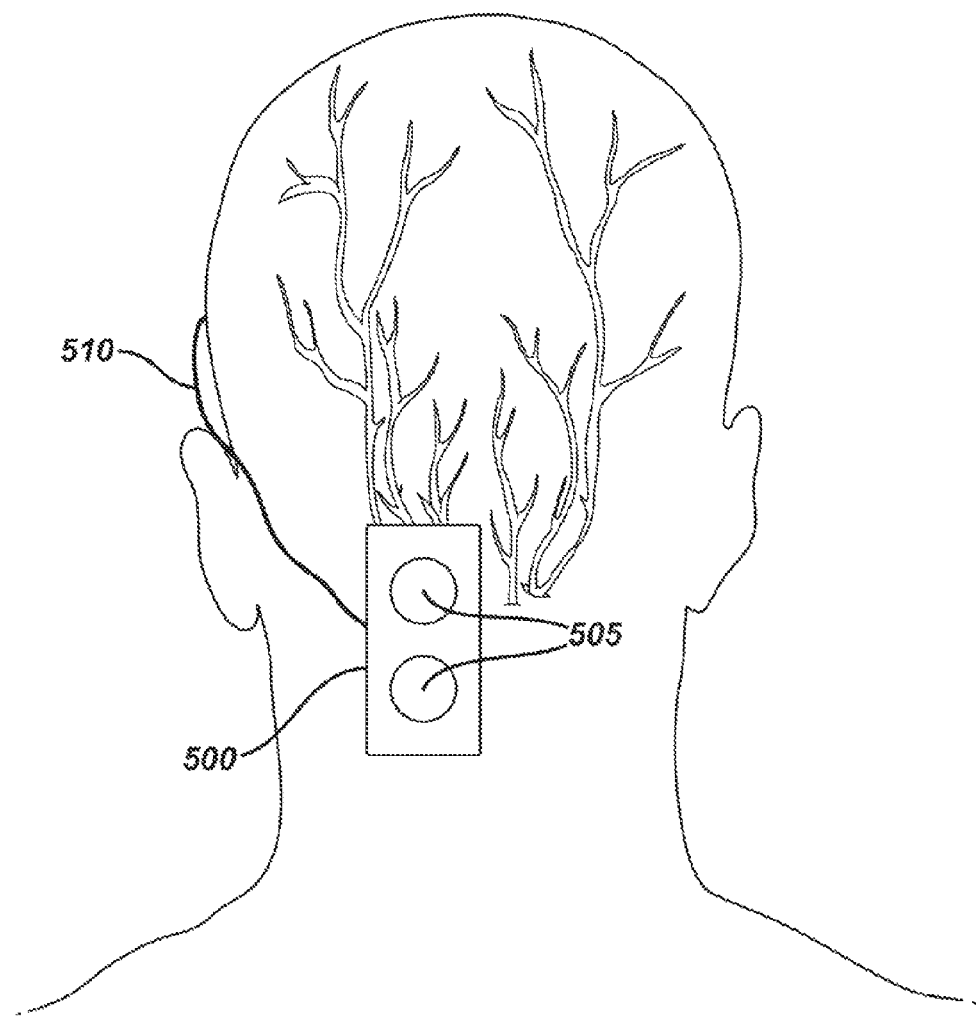
FIG. 5C is an alternative substantially vertical orientation of the patch for stimulation of the occipital nerve in accordance with the present inventive transcutaneous external electrical stimulator system for simultaneous electrical stimulation of the occipital and trigeminal nerves.

Specifically, FIG. 5A is back view of the head of the human body of the present inventive system for transcutaneous electrical stimulation of the occipital nerve (or one of its branches) and trigeminal nerves (or one of its superficial branches, for example, opthamalic nerve, supraorbital nerve, supratrochlear nerve, infratrochlear nerve, maxillary nerve, zygomatic nerve, zygomaticotemporal nerve, zygomaticofacial nerve, infraorbital nerve, anterior superior alveolar nerve, mandibular nerve and auriculotemporal nerve) with the patch disposed to stimulate the occipital nerve oriented in a substantially horizontal direction. One transcutaneous electrical stimulator patch 500 is disposed on the back of the head to stimulate the occipital nerve or one of its branches. In the illustrated example shown in FIG. 5A patch 500 is oriented in a substantially horizontal direction; however, the orientation of the patch 500 may be modified, as desired, for example, in a substantially vertical direction as seen in FIG. 5C. Patch 500 includes one or more electrodes 505, preferably a pair of electrodes, and electronic circuitry such as an implantable pulse generator and a battery. An opposite front view, depicted in FIG. 5B, shows the second transdermal electrical stimulation patch 515 positioned on the front of the head above the eye to stimulate the trigeminal nerve or one of its superficial branches (TNS—trigeminal nerve stimulation). The two patches 500, 515 may either be the same or differ in number of electrodes therein. In FIGS. 5A & 5B the two patches 500, 515 are similarly oriented on the head in a substantially horizontal direction. As desired, the orientation of the two patches 500, 515 may be arranged so that they are the same or differ from one another. By way of example, the patch disposed on the back of the head may be oriented in a substantially vertical direction, as shown in FIG. 5C, to stimulate the occipital nerve or one of its branches. Patches 500 and 515 are electrically connected to one another via a wired interface 510. Otherwise, a wireless communication interface may be provided between the two patches. Unilateral stimulation on either the left or right sides of the body is contemplated as well as bilateral stimulation, depending on the identified areas of pain.

One challenge associated with the stimulation of the ONS and/or TNS nerves is that these nerves are stimulated by relative low frequency signals, on the order of approximately 1 Hz-approximately 200 Hz. However, the scalp includes superficial layers such as: skin, fat, fibrous and dense connective tissue, and areolar connective tissue. Inherent impedance associated with the scalp hampers the stimulation signal within this frequency range from passing through body tissue. Skin impedance may be overcome by modulating the stimulation signal by a higher frequency carrier waveform signal preferably in the range of approximately 100 kHz-approximately 400 kHz, as described in detail in the commonly assigned U.S. Pat. No. 7,979,137 which is herein incorporated by reference in its entirety. The higher frequency carrier enables the lower frequency stimulation signal to bypass the impedance associated with the superficial (fat and connective tissue) layers of the scalp while the envelope of the lower frequency stimulation signal initiates an action potential that stimulates the occipital nerves and/or trigeminal nerves or its associated branches.

Figure 14A:
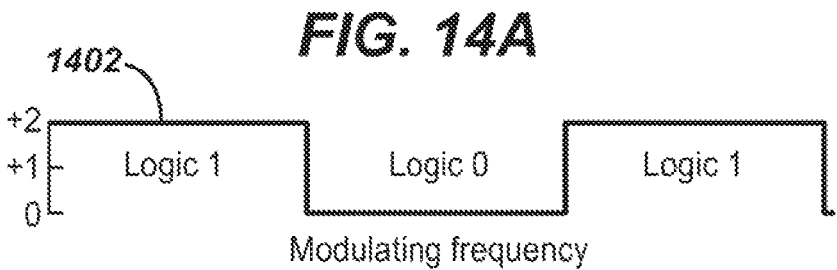
FIGS. 14A-14C illustrates exemplary waveforms generated by the electronic circuitry in FIG. 13.
Figure 14B:
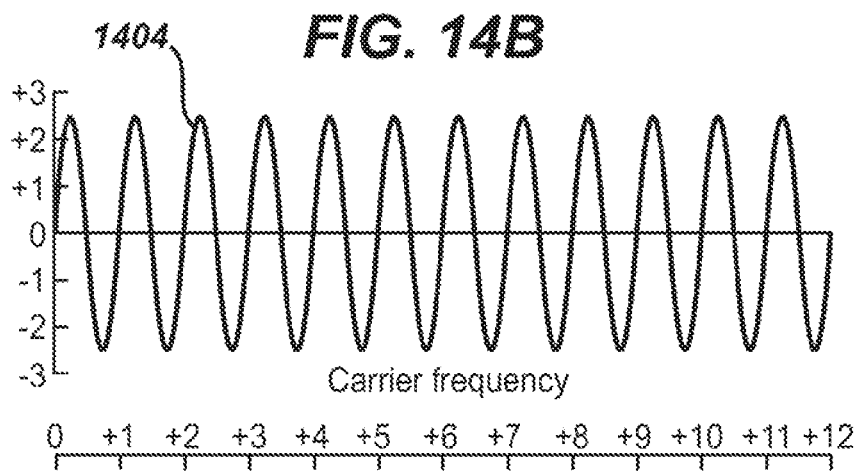
Figure 14C:
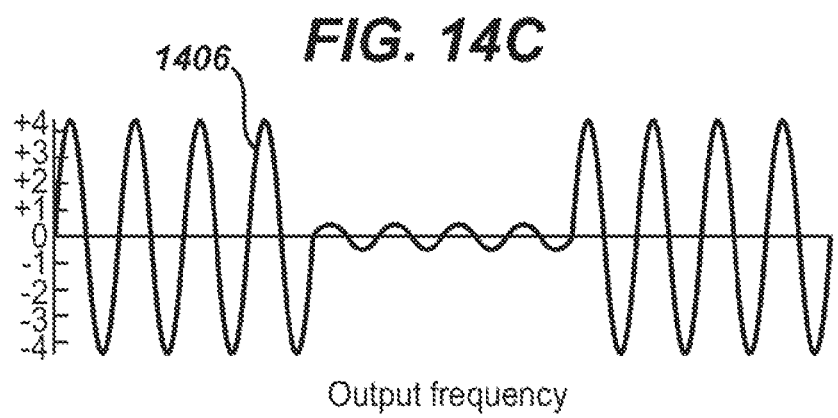

FIG. 13 illustrates schematically an exemplary transdermal signal transmitter 1300 preferably integrated within the transdermal electrical patch in accordance with the present invention. Signal transmitter 1300 includes a power source 1302 such as a lithium ion film batter, a first waveform generator 1304 and a second 1306 waveform generator, each electrically connected to be powered by the battery. Waveform generators 1304, 1306 may be of any suitable type, such as those sold by Texas Instruments of Dallas. Tex. under model number NE555. The first waveform generator 1304 generates a first waveform or signal having a frequency known to stimulate the targeted nerve in the body, for example, the occipital nerve or trigeminal nerve, which is approximately within the range of approximate 1 Hz-approximately 200 Hz. As indicated above, such a stimulation signal within this frequency range when applied to the skin, in and of itself, cannot pass through body tissue to reach the occipital and/or trigeminal nerves and associated branches with sufficient current density to stimulate the target nerve. Thus, the second waveform generator 1306 is provided to generate a carrier waveform, which is applied along with the first waveform to an amplitude modulator 1308, such as an On-Semi MC 1496 modulator by Texas Instruments. The first waveform is preferably a square wave having a frequency of approximately 1 Hz-approximately 100 Hz, and the second waveform is preferably a sinusoidal signal having a frequency in the range of approximately 20 KHz-approximately 500 KHz. Modulation of the first waveform 1402 (FIG. 14A) with the second waveform (carrier wave) 1404 (FIG. 14B) results in a modulated waveform or signal 1406 having generally the configuration shown in FIG. 14C.

The modulated signal 1406 is provided to an appropriate surface electrode 1310, such as DURA-STICK Self Adhesive Electrodes from Chattanooga Group, Inc. of Hixson, Tenn., that applies the modulated waveform directly to the skin. The use of the modulated signal enables transmission of the waveform through tissue due to the relatively high frequency nature of the first waveform, yet allows it to be detected (and responded to) by the occipital and/or trigeminal nerve and associated branches due to the relatively low frequency envelope of the modulated signal.

Figure 6A:
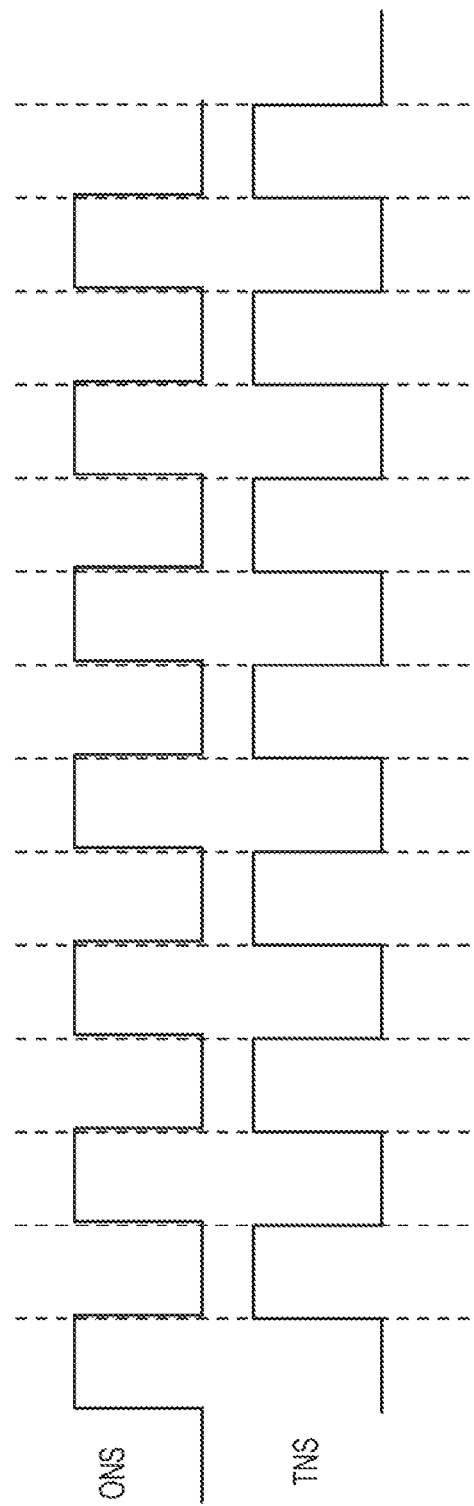
FIGS. 6A & 6B are respective continuous and intermittent stimulation timing diagrams for ONS and TNS waveforms.
Figure 6B:
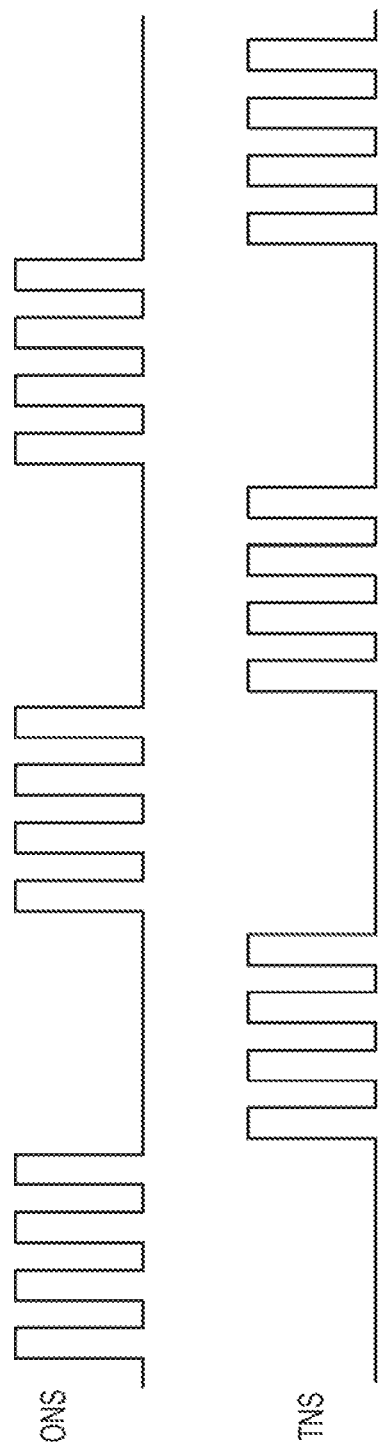

Stimulation of the occipital and trigeminal nerves may be continuous or intermittent in the time domain. Several exemplary timing diagrams are depicted in FIGS. 6A & 6B. In particular, FIG. 6A shows a continuous but staggered electrical stimulation is applied to the ONS and TNS nerves (or respective associated branches of each). The upper waveform (ONS waveform) is provided to patch 500 (FIG. 5A) and the lower waveform (TNS waveform) applied to patch 515 (FIG. 5B) together provide simultaneous continuous electrical stimulation staggered relative to one another in the time domain. An alternative timing diagram is depicted in FIG. 6B in which the waveform in which intermittent staggered electrical stimulation to the ONS and TNS nerves is provided. The exemplary timing diagrams of the ONS and TNS waveforms depicted in each of FIGS. 6A & 6B are both staggered (asynchronous) relative to one another. It is contemplated and within the intended scope of the present invention for the waveforms to be simultaneously applied (synchronous).

The duty cycle of each waveform is preferably adjustable for optimum therapeutic treatment and conserve energy. The stimulation circuit may be either voltage or current controlled.

Placement of the patches 500, 515 on the head to stimulate the ONS and TNS nerves, respectively, may be realized based on stimulation induced paresthesia using a grid (as described in detail above with respect to FIGS. 2A & 2B) or an anatomical reference physical positioning device (in accordance with the embodiments depicted in FIGS. 4A; 4B; 5A; 5B). Other conventional methods for positioning of transdermal patches on the head to electrically stimulate the ONS and TNS may be utilized in connection with the present invention.

In the illustrative examples, the amplitude of the respective ONS and TNS waveforms are substantially equal. It is contemplated and within the intended scope of the present invention for the amplitudes of the respective waveforms to differ from one another.

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. A device for providing transdermal electrical stimulation at an adjustable position on a head, comprising:
   at least one pair of electrodes for producing the transdermal electrical stimulation; and
   a securing member shaped and configured to be releasably securable only about a plurality of strands of hair at a predetermined fixed orientation without being secured about any anatomical body part; the at least one pair of electrodes being mounted to the securing member;
   wherein the securing member comprises:
   a flexible substrate having at least two openings defined therein, the at least one pair of electrodes being mounted to the flexible substrate; and
   a rod insertable through the at least two openings for releasably securing the plural strands of hair between the flexible substrate and the rod to retain the device at the predetermined fixed orientation about the head.

2. The device in accordance with claim 1, further comprising a plurality of non-conductive bristles exclusively for securing the flexible substrate to the plural strands of hair.

3. The device in accordance with claim 2, wherein the plural non-conductive bristles do not provide electrical stimulation or move the plural strands of hair away to provide contact at an interface between the at least one pair of electrodes and the head.

4. The device in accordance with claim 2, wherein the plural non-conductive bristles are filed with hydrogel that is releasable when subject to application of a sufficient force.

5. The device in accordance with claim 1, wherein the securing member is shaped as a spring loaded hair clip.

6. The device in accordance with claim 5, wherein the spring loaded clip is a butterfly clip with intermeshed mating teeth and electrode pairs are disposed proximate tips of at least some of the intermeshed mating teeth.

7. The device in accordance with claim 1, wherein the securing member is shaped as a barrette.

\* \* \* \* \*